US011493496B2

(12) United States Patent
Bai et al.

(10) Patent No.: US 11,493,496 B2
(45) Date of Patent: Nov. 8, 2022

(54) METHOD AND SYSTEM FOR ESTIMATING SURFACE RUNOFF BASED ON PIXEL SCALE

(71) Applicant: Institute of Geochemistry, Chinese Academy of Sciences, Guiyang (CN)

(72) Inventors: Xiaoyong Bai, Guiyang (CN); Shijie Wang, Guiyang (CN); Luhua Wu, Guiyang (CN); Fei Chen, Guiyang (CN); Miao Zhou, Guiyang (CN); Yichao Tian, Guiyang (CN); Guangjie Luo, Guiyang (CN); Qin Li, Guiyang (CN); Jinfeng Wang, Guiyang (CN); Yuanhuan Xie, Guiyang (CN); Yujie Yang, Guiyang (CN); Chaojun Li, Guiyang (CN); Yuanhong Deng, Guiyang (CN); Zeyin Hu, Guiyang (CN); Shiqi Tian, Guiyang (CN); Qian Lu, Guiyang (CN); Chen Ran, Guiyang (CN); Min Liu, Guiyang (CN)

(73) Assignee: Institute of Geochemistry, Chinese Academy of Sciences, Guiyang (CN)

(*) Notice: Subject to any disclaimer, the term of this patent is extended or adjusted under 35 U.S.C. 154(b) by 314 days.

(21) Appl. No.: 16/863,884

(22) Filed: Apr. 30, 2020

(65) Prior Publication Data
US 2021/0341454 A1 Nov. 4, 2021

(51) Int. Cl.
*G06K 9/00* (2022.01)
*G01N 33/24* (2006.01)
(Continued)

(52) U.S. Cl.
CPC ....... *G01N 33/246* (2013.01); *G01N 33/0098* (2013.01); *G01W 1/00* (2013.01);
(Continued)

(58) Field of Classification Search
None
See application file for complete search history.

(56) References Cited

U.S. PATENT DOCUMENTS 11,300,709 B2 * 4/2022 Bai .................. G06F 17/11

OTHER PUBLICATIONS

Simic et al., "Assessing the impact of leaf area index on evapotranspiration and groundwater recharge across a shallow water region for diverse land cover and soil properties", 2014 (Year: 2014).*

* cited by examiner

*Primary Examiner* — Soo Jin Park
(74) *Attorney, Agent, or Firm* — Avek IP, LLC

(57) ABSTRACT

Methods and systems for estimating a surface runoff based on a pixel scale are disclosed. In some embodiments, the method includes the following steps: (1) calculating a vegetation canopy interception water storage, a litterfall interception water storage, and a soil water storage according to an obtained original remote sensing dataset of a climate element in a study area; (2) calculating a vegetation-soil interception water conservation in the study area based on an established vegetation-soil interception water conservation estimation model according to the vegetation canopy interception water storage, the litterfall interception water storage, the soil water storage, and monthly precipitation; and (3) calculating a surface runoff in the study area based on an established water balance water conservation estimation model according to the monthly precipitation, monthly snowmelt, monthly actual evapotranspiration, and the vegetation-soil interception water conservation in the study area.

8 Claims, 2 Drawing Sheets

(51) Int. Cl.
　　　*G01W 1/00* 　　　(2006.01)
　　　*G06T 7/62* 　　　(2017.01)
　　　*G01N 33/00* 　　(2006.01)
(52) U.S. Cl.
　　　CPC ...... *G06T 7/62* (2017.01); *G06T 2207/10032* (2013.01); *G06T 2207/30181* (2013.01)

METHOD AND SYSTEM FOR ESTIMATING SURFACE RUNOFF BASED ON PIXEL SCALE

FIELD OF THE DISCLOSURE

The disclosure relates generally to environment monitoring and surface and groundwater resource utilization. More specifically, the disclosure relates to methods and systems for estimating a surface runoff based on a pixel scale.

BACKGROUND

Surface runoff is an important part of available water resources for maintaining ecological balance and promoting human society development. The current estimation of surface runoff mainly depends on three methods: river section and water system monitoring, land water balance equation estimation, and rainfall-runoff coefficient method estimation model. The river section and water system monitoring have a relatively small range and a large difficulty. As a result, such monitoring can only obtain regional or local point-to-area runoff characteristics. The land water balance equation can only obtain regional or watershed-based total runoff characteristics. Due to the significant spatial heterogeneity of a runoff coefficient, the rainfall-runoff coefficient estimation method has a large difficulty to monitor and relies only on the experimental monitoring of a point-based surface runoff coefficient to estimate a point-based surface runoff. Therefore, the traditional methods are difficult to apply to a large-scale study area or a local space in terms of scale and method.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, the disclosure provides a method for estimating a surface runoff based on a pixel scale. The method includes the following steps.

(1) Obtaining an original remote sensing dataset of a climate element in a study area. The original remote sensing dataset of the climate element includes monthly precipitation, monthly actual evapotranspiration, monthly soil water content, monthly snowmelt, monthly soil thickness, and monthly leaf area index.

(2) Calculating a vegetation canopy interception water storage, a litterfall interception water storage, and a soil water storage based on the original remote sensing dataset of the climate element.

(3) Calculating a vegetation-soil interception water conservation in the study area based on an established vegetation-soil interception water conservation estimation model according to the vegetation canopy interception water storage, the litterfall interception water storage, the soil water storage, and the monthly precipitation. The vegetation-soil interception water conservation estimation model is established by adding up the vegetation canopy interception water storage, the litterfall interception water storage, and the soil water storage, and comparing with the monthly precipitation.

(4) Calculating a surface runoff in the study area based on an established water balance water conservation estimation model according to the monthly precipitation, the monthly snowmelt, the monthly actual evapotranspiration, and the vegetation-soil interception water conservation in the study area. The water balance water conservation model is established by separately subtracting the monthly actual evapotranspiration and the surface runoff in sequence from a sum of the monthly precipitation and the monthly snowmelt.

Optionally, the method further includes step (1a) of preprocessing data in the original remote sensing dataset of the climate element to obtain a processed dataset of the climate element in the study area after step (1). The preprocessing includes at least one operation step selected from the group consisting of format conversion, image correction, cropping, registration, quality inspection, and projection conversion.

Optionally, step (2) further includes following steps (21)-(23).

(21) Calculating the vegetation canopy interception water storage according to the following equation.

$$CWS = F_C \times LAI \times H_{SV}$$

Here, CWS is the vegetation canopy interception water storage and is measured in mm, $H_{SV}$ is the average maximum water holding depth per leaf area and is measured in mm, $F_C$ is the vegetation coverage in the processed dataset of the climate element, and LAI is the leaf area index in the processed dataset of the climate element.

(22) Calculating the litterfall interception water storage according to the following equation.

$$CIS = (0.085 R_m - 0.1 R_0) \times M$$

Here, CIS is the litterfall interception water storage and is measured in mm, $R_0$ is the average natural water content of vegetation in g/kg, $R_m$ is the maximum water holding capacity of vegetation in g/kg, and M is the litterfall accumulation in t/hm$^2$.

(23) determining that the monthly soil water content in the processed dataset of the climate element is used as the soil water storage.

Optionally, step (3) includes calculating the vegetation-soil interception water conservation in the study area by inputting the vegetation canopy interception water storage, the litterfall interception water storage, the soil water storage, and the monthly precipitation in the processed dataset of the climate element into the established vegetation-soil interception water conservation estimation model. The vegetation-soil interception water conservation estimation model uses the following equations.

$$V_{max} = CWS + CIS + SMS$$

$$\begin{cases} Q_{WC} = V_{max} & P_i \geq V_{max} \\ Q_{WC} = P_i & P_i < V_{max} \end{cases},$$

Here, $V_{max}$ is the maximum forest interception water storage and is measured in mm, CWS is the vegetation canopy interception water storage and is measured in mm, CIS is the litterfall interception water storage and is measured in mm, SMS is the soil water storage and is measured in mm, $Q_{WC}$ is the vegetation-soil interception water conservation and is measured in mm, and $P_i$ is precipitation in an i month and is measured in mm.

Optionally, step (4) includes calculating the surface runoff in the study area by inputting the monthly precipitation in the processed dataset of the climate element, the monthly snowmelt in the processed dataset of the climate element, the monthly actual evapotranspiration in the processed dataset of the climate element, and the vegetation-soil interception water conservation in the study area into the water balance water conservation estimation model. The water balance water conservation model uses the following equation.

$$Q_{WC}=Q_{SN}+P-E-R_{Surface}$$

Here, $Q_{WC}$ is the vegetation-soil interception water conservation and is measured in mm, P is the monthly precipitation and is measured in mm, E is the monthly actual evapotranspiration and is measured in mm, $R_{Surface}$ is the surface runoff and is measured in mm, and $Q_{SN}$ is the monthly snowmelt and is measured in mm.

In other embodiments, the disclosure provides a system for estimating a surface runoff based on a pixel scale. The system includes a climate element original remote sensing dataset obtaining module, a correlation factor calculation module, a study area vegetation-soil interception water conservation calculation module, and a study area surface runoff calculation module.

The climate element original remote sensing dataset obtaining module is configured to obtain an original remote sensing dataset of a climate element in a study area. The original remote sensing dataset of the climate element comprises monthly precipitation, monthly actual evapotranspiration, monthly soil water content, monthly snowmelt, monthly soil thickness, and monthly leaf area index.

The correlation factor calculation module is configured to calculate a vegetation canopy interception water storage, a litterfall interception water storage, and a soil water storage based on the original remote sensing dataset of the climate element.

The study area vegetation-soil interception water conservation calculation module is configured to calculate a vegetation-soil interception water conservation in the study area based on an established vegetation-soil interception water conservation estimation model according to the vegetation canopy interception water storage, the litterfall interception water storage, the soil water storage, and the monthly precipitation. The vegetation-soil interception water conservation estimation model is established by adding up the vegetation canopy interception water storage, the litterfall interception water storage, and the soil water storage, and comparing with the monthly precipitation.

The study area surface runoff calculation module is configured to calculate a surface runoff in the study area based on an established water balance water conservation estimation model according to the monthly precipitation, monthly snowmelt, monthly actual evapotranspiration, and the vegetation-soil interception water conservation in the study area. The water balance water conservation model is established by separately subtracting the monthly actual evapotranspiration and the surface runoff in sequence from a sum of the monthly precipitation and the monthly snowmelt.

Optionally, the system further includes a preprocessing module configured to preprocess data in the original remote sensing dataset of the climate element to obtain a processed dataset of the climate element in the study area. The preprocessing includes at least one operation step selected from the group consisting of format conversion, image correction, cropping, registration, quality inspection, and projection conversion.

Optionally, the relation factor calculation module includes a vegetation canopy interception water storage calculation unit configured to calculate the vegetation canopy interception water storage according to the following equation.

$$CWS=F_C\times LAI\times H_{SV}$$

Here, CWS is the vegetation canopy interception water storage and is measured in mm, $H_{SV}$ is the average maximum water holding depth per leaf area and is measured in mm, $F_C$ is the vegetation coverage in the processed dataset of the climate element, and LAI is the leaf area index in the processed dataset of the climate element.

Optionally, the relation factor calculation module includes a litterfall interception water storage calculation unit configured to calculate the litterfall interception water storage according to the following equation.

$$CIS=(0.085R_m-0.1R_0)\times M$$

Here, CIS is the litterfall interception water storage and is measured in mm, $R_0$ is the average natural water content of vegetation in g/kg, is the maximum water holding capacity of vegetation in g/kg, and M is the litterfall accumulation in t/hm².

Optionally, the relation factor calculation module includes a soil water storage determination unit configured to determine that the monthly soil water content in the processed dataset of the climate element is used as the soil water storage.

Optionally, the study area vegetation-soil interception water conservation calculation module includes a study area vegetation-soil interception water conservation calculation unit configured to calculate the vegetation-soil interception water conservation in the study area by inputting the vegetation canopy interception water storage, the litterfall interception water storage, the soil water storage, and the monthly precipitation in the processed dataset of the climate element into the established vegetation-soil interception water conservation estimation model. The vegetation-soil interception water conservation estimation model uses the following equations.

$$V_{max}=CWS+CIS+SMS$$
$$\begin{cases} Q_{WC}=V_{max} & P_i \geq V_{max} \\ Q_{WC}=P_i & P_i < V_{max} \end{cases}$$

Here, $V_{max}$ is the maximum forest interception water storage and is measured in mm, CWS is the vegetation canopy interception water storage and is measured in mm, CIS is the litterfall interception water storage and is measured in mm, SMS is the soil water storage and is measured in mm, $Q_{WC}$ is the vegetation-soil interception water conservation and is measured in mm, and $P_i$ is precipitation in an i month and is measured in mm.

Optionally, the study area surface runoff calculation module includes a study area surface runoff calculation unit configured to calculate the surface runoff in the study area by inputting the monthly precipitation in the processed dataset of the climate element, the monthly snowmelt in the processed dataset of the climate element, the monthly actual evapotranspiration in the processed dataset of the climate element, and the vegetation-soil interception water conservation in the study area into the water balance water conservation estimation model. The water balance water conservation model uses the following equation:

$$Q_{WC}=Q_{SN}+P-E-R_{Surface}$$

Here, $Q_{WC}$ is the vegetation-soil interception water conservation and is measured in mm, P is the monthly precipitation and is measured in mm, E is the monthly actual evapotranspiration and is measured in mm, $R_{Surface}$ is the surface runoff and is measured in mm, and $Q_{SN}$ is the monthly snowmelt and is measured in mm.

BRIEF DESCRIPTION OF THE DRAWINGS

Illustrative embodiments of the present disclosure are described in detail below with reference to the figures.

DETAILED DESCRIPTION

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

Figure 1:
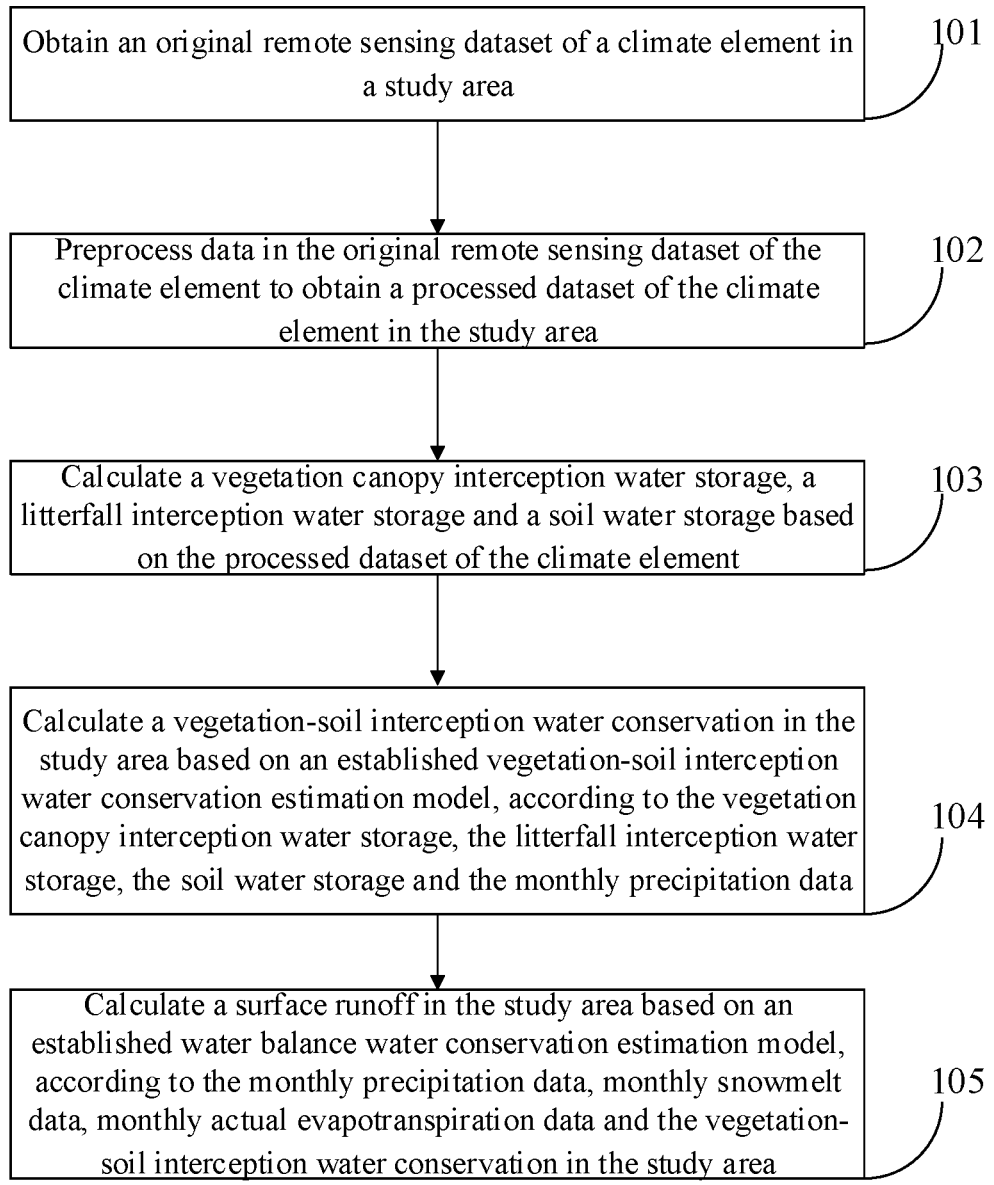
FIG. 1 is a flowchart illustrating a method for estimating a surface runoff based on a pixel scale according to an embodiment of the disclosure.

FIG. 1 is a flowchart illustrating a method for estimating a surface runoff based on a pixel scale according to an embodiment of the disclosure. As shown in FIG. 1, the disclosure may provide a method for estimating a surface runoff based on a pixel scale including following steps 101-104.

Step 101. Obtain an original remote sensing dataset of a climate element in a study area. The original remote sensing dataset of the climate element may include monthly precipitation, monthly actual evapotranspiration, monthly soil water content, monthly snowmelt, monthly soil thickness, normalized difference vegetation index (NDVI), vegetation coverage, and leaf area index, et cetera.

The original remote sensing dataset of the climate element may include the following monthly data: precipitation; actual evapotranspiration; soil water content at thicknesses of 0-10 cm, 10-40 cm, 40-100 cm, and 100-200 cm; and snowmelt, which may be merged into annual data. These data may be derived from a FLDAS dataset (FLDAS Noah Land Surface Model L4 Global Monthly 0.1×0.1 degree (MERRA-2 and CHIRPS) V001 (FLDAS_NOAH01_C_GL_M) at GES DISC (https://ldas.gsfc.nasa.gov/FLDAS/)) of National Aeronautics and Space Administration (NASA) (https://www.nasa.gov/). The FLDAS dataset may have a spatial resolution of 0.1°×0.1°. These data may also be derived from a GLDAS dataset. The original remote sensing dataset of the climate element may have a monthly time resolution and a global spatial coverage (60S, 180W, 90N and 180E).

In addition, global soil depth may be used to calculate the monthly soil thickness. The global soil depth may be derived from https://daac.ornl.gov/, with a spatial resolution of 0.1°× 0.1°, and https://www.isric.org/explore/soilgrids. Soil depth with different spatial resolutions (e.g., 250 m×250 m, 1 km×1 km, 5 km×5 km, and 10 km×10 km) may also be selected according to a research scale. The latest administrative division vector data in 2015 may be derived from the Resource and Environment Data Cloud Platform of the Chinese Academy of Sciences (http://www.resdc.cn/) and the National Bureau of Surveying, Mapping, and Geographic Information (http://www.sb sm.gov.cn/article/zxbs/dtfw/).

The other vegetation parameters may be derived from literature reference. The NDVI used to calculate the vegetation coverage and the leaf area index (LAI) data used to calculate the vegetation canopy interception water storage may be derived from a medium-resolution MODIS13Q1NDVI dataset released by NASA.

Global land snowmelt may be derived from Global Land Data Assimilation System (GLDAS), the Goddard Earth Sciences Data and Information Services Center (GES DISC), GLDAS Noah Land Surface Model L4 Monthly 0.25×0.25 degree. (https://mirador.gsfc.nasa.gov/).

Step 102. Preprocessing data in the original remote sensing dataset of the climate element to obtain a processed dataset of the climate element in the study area. The preprocessing may include at least one operation steps selected from the group consisting of format conversion, image correction, cropping, registration, quality inspection, and projection conversion. Optionally, the preprocessing may include operation steps of format conversion, image correction, cropping, registration, quality inspection, and projection conversion in sequence.

The disclosure may utilize a data assimilation method to convert a grid cell size of all raster data in the original remote sensing dataset of the climate element to the same scale. The projection method may be Albers Equal-area Conic Projection (Krasovsky-1940-Albers), which is a projected coordinate system.

The above-mentioned global scale raster data may be processed by format conversion, image correction, cropping, registration, quality inspection, and projection conversion to finally obtain a processed dataset of the climate element in the study area.

The vegetation canopy interception water storage, the litterfall interception water storage, and the soil water storage may be calculated based on the processed dataset of the climate element. Finally, the surface runoff may be calculated by two water conservation calculation models.

Step 103. Calculating a vegetation canopy interception water storage, a litterfall interception water storage, and a soil water storage based on the processed dataset of the climate element.

The vegetation canopy interception water storage may be calculated according to an average maximum water holding depth per leaf area, the vegetation coverage, and the leaf area index. The average maximum water holding depth per leaf area may be determined according to an empirical value based on literature reference and different vegetation types.

The vegetation canopy interception water storage may be calculated by the following equation (1).

$$CWS = F_C \times LAI \times H_{SV} \qquad (1)$$

In the above equation (1), CWS is the vegetation canopy interception water storage and is measured in mm, $H_{SV}$ is the average maximum water holding depth per leaf area and is measured in mm, $F_C$ is the vegetation coverage in the processed dataset of the climate element, and LAI is the leaf area index in the processed dataset of the climate element.

The litterfall interception water storage may be calculated based on an average natural water content of vegetation, a maximum water holding capacity of vegetation, and a litterfall accumulation. The liter interception may be calculated may be calculated by the following equation (2):

$$CIS = (0.085 R_m - 0.1 R_0) \times M \qquad (2)$$

In the above equation (2), CIS is the litterfall interception water storage and is measured in mm, $R_0$ is the average natural water content of vegetation in g/kg, $R_m$ is the maximum water holding capacity of vegetation in g/kg, and M is the litterfall accumulation in t/hm². The average natural water content of vegetation, the maximum water holding capacity of vegetation and the liter accumulation may be determined according to an empirical value based on a literature and different vegetation types.

The soil water storage of the disclosure is not calculated by a traditional method of multiplying a soil thickness (which may take a value of 0.4 m) by a non-capillary porosity, but may directly use the remote sensing data of the soil water content. Specifically, the soil water storage may use preprocessed soil water content (soil depth 2 m), derived from the FLDAS dataset (FLDAS Noah Land Surface Model L4 Global Monthly 0.1×0.1 degree (MERRA-2 and CHIRPS) V001 (FLDAS_NOAH01_C_GL_M) at GES DISC (https://ldas.gsfc.nasa.gov/FLDAS/)) of NASA (https://www.nasa.gov/), with a spatial resolution of 0.1°× 0.1°.

Step 104. Calculating a vegetation-soil interception water conservation in the study area based on an established vegetation-soil interception water conservation estimation model according to the vegetation canopy interception water storage, the litterfall interception water storage, the soil water storage, and the monthly precipitation. The vegetation-soil interception water conservation estimation model may be established by adding up the vegetation canopy interception water storage, the litterfall interception water storage, and the soil water storage, and comparing with the monthly precipitation.

The vegetation-soil interception water conservation estimation model may include the following equations (3) and (4).

$$V_{max} = CWS + CIS + SMS \qquad (3)$$
$$= F_C \times LAI \times H_{SV} + (0.085R_m - 0.1R_0) \times M + SMS$$

$$\begin{cases} Q_{WC} = V_{max} & P_i \geq V_{max} \\ Q_{WC} = P_i & P_i < V_{max} \end{cases} \qquad (4)$$

In the above equations (3) and (4), $V_{max}$ is the maximum forest interception water storage water storage and is measured in mm, CWS is the vegetation canopy interception water storage and is measured in mm, CIS is the litterfall interception water storage and is measured in mm, SMS is the soil water storage and is measured in mm, $Q_{WC}$ is the vegetation-soil interception water conservation and is measured in mm, and $P_i$ is precipitation in an i month and is measured in mm.

When the precipitation in the i month exceeds the maximum forest interception water storage water storage, the vegetation-soil interception water conservation is the maximum forest interception water storage water storage. When the precipitation in the i month is less than the maximum forest interception water storage, the vegetation-soil interception water conservation is the precipitation in the i month.

Step 105. Calculating a surface runoff in the study area based on an established water balance water conservation estimation model according to the monthly precipitation, monthly snowmelt, monthly actual evapotranspiration, and the vegetation-soil interception water conservation in the study area. The water balance water conservation model may be established by separately subtracting the monthly actual evapotranspiration and the surface runoff in sequence from a sum of the monthly precipitation and the monthly snowmelt based on water input and output in the perspective of water balance.

The water balance water conservation model may include the following equation (5).

$$Q_{WC} = Q_{SN} + P - E - R_{Surface} \qquad (5)$$

In the above equation (5), $Q_{WC}$ is the vegetation-soil interception water conservation and is measured in mm, P is the monthly precipitation and is measured in mm, E is the monthly actual evapotranspiration and is measured in mm, $R_{surface}$ is the surface runoff and is measured in mm, and $Q_{SN}$ is the monthly snowmelt and is measured in mm.

The snowmelt may be derived from resampling of global (60S, 180W, 90N, 180E) monthly snowmelt with a spatial resolution of 0.125°×0.125°. The above-mentioned monthly snowmelt may be derived from the NLDAS dataset (Noah Land Surface Model L4 Monthly 0.125×0.125°, https://mirador.gsfc.nasa.gov/).

The surface runoff may be calculated by the following equation (6).

$$R_{Surface} = QSN + P - E - Q_{WC} \qquad (6)$$
$$= Q_{SN} + P - (E + F_C \times LAI \times H_{SV} +$$
$$(0.085R_m - 0.1R_0) \times M + SMS)$$

In the above equation (6), $Q_{WC}$ is the vegetation-soil interception water conservation and is measured in mm, P is the monthly precipitation and is measured in mm, E is the monthly actual evapotranspiration and is measured in mm, $R_{surface}$ is the surface runoff and is measured in mm, and $Q_{SN}$ is the monthly snowmelt in the processed dataset of the climate element and is measured in mm.

Figure 2:
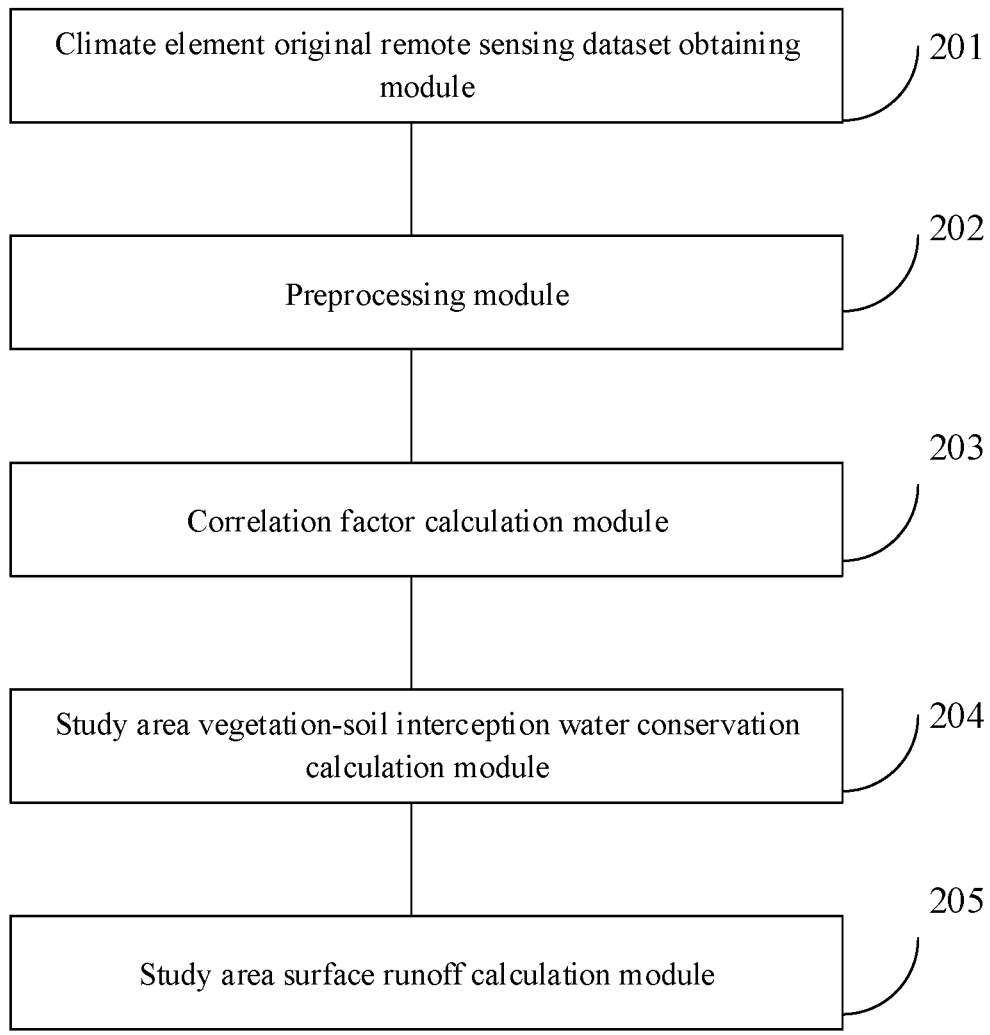
FIG. 2 is a structural diagram illustrating a system for estimating a surface runoff based on a pixel scale according to an embodiment of the disclosure.

FIG. 2 is a structural diagram illustrating a system for estimating a surface runoff based on a pixel scale according to an embodiment of the disclosure. As shown in FIG. 2, the disclosure may provide a system for estimating a surface runoff based on a pixel scale. The system may include a climate element original remote sensing dataset obtaining module 201, a preprocessing module 202, a correlation factor calculation module 203, a study area vegetation-soil interception water conservation calculation module 204, and a study area surface runoff calculation module 205.

The climate element original remote sensing dataset obtaining module 201 may be configured to obtain an original remote sensing dataset of a climate element in a study area. The original remote sensing dataset of the climate element may include monthly precipitation, monthly actual evapotranspiration, monthly soil water content, monthly snowmelt, monthly soil thickness, normalized difference vegetation index (NDVI), vegetation coverage, leaf area index, et cetera.

The preprocessing module 202 may be configured to preprocess data in the original remote sensing dataset of the climate element to obtain a processed dataset of the climate element in the study area. The preprocessing may include at least one operation step selected from the group consisting of format conversion, image correction, cropping, registration, quality inspection, and projection conversion. Optionally, the preprocessing may include the operation steps of format conversion, image correction, cropping, registration, quality inspection, and projection conversion in sequence.

The correlation factor calculation module 203 may be configured to calculate a vegetation canopy interception water storage, a litterfall interception water storage, and a soil water storage based on the original remote sensing dataset of the climate element.

The study area vegetation-soil interception water conservation calculation module 204 may be configured to calculating a vegetation-soil interception water conservation in the study area based on an established vegetation-soil interception water conservation estimation model according to the vegetation canopy interception water storage, the litterfall interception water storage, the soil water storage, and the monthly precipitation. The vegetation-soil interception water conservation estimation model may be established by adding up the vegetation canopy interception water storage, the litterfall interception water storage, and the soil water storage, and comparing with the monthly precipitation.

The study area surface runoff calculation module 205 may be configured to calculate a surface runoff in the study area based on an established water balance water conservation estimation model according to the monthly precipitation, monthly snowmelt, monthly actual evapotranspiration, and the vegetation-soil interception water conservation in the study area. The water balance water conservation model may be established by separately subtracting the monthly actual evapotranspiration and the surface runoff in sequence from a sum of the monthly precipitation and the monthly snowmelt.

The correlation factor calculation module 203 may include a vegetation canopy interception water storage calculation unit, a litterfall interception water storage calculation unit, and a soil water storage determination unit.

The vegetation canopy interception water storage calculation unit may be configured to calculate the vegetation canopy interception water storage according to the following equation (7).

$$CWS = F_C \times LAI \times H_{SV} \qquad (7)$$

In the above equation (7), CWS is the vegetation canopy interception water storage and is measured in mm, $H_{SV}$ is the average maximum water holding depth per leaf area and is measured in mm, $F_C$ is the vegetation coverage in the processed dataset of the climate element, and LAI is the leaf area index in the processed dataset of the climate element.

The litterfall interception water storage calculation unit may be configured to calculate the litterfall interception water storage according to the following equation (8).

$$CIS = (0.085R_m - 0.1R_0) \times M \qquad (8)$$

In the above equation (8), CIS is the litterfall interception water storage and is measured in mm, $R_0$ is the average natural water content of vegetation in g/kg, $R_m$ is the maximum water holding capacity of vegetation in g/kg, and M is the litterfall accumulation in t/hm²

The soil water storage determination unit may be configured to determine that the monthly soil water content in the processed dataset of the climate element is used as the soil water storage.

The study area vegetation-soil interception water conservation calculation module 204 may include a study area vegetation-soil interception water conservation calculation unit configured to calculate the vegetation-soil interception water conservation in the study area by inputting the vegetation canopy interception water storage, the litterfall interception water storage, the soil water storage, and the monthly precipitation in the processed dataset of the climate element into the established vegetation-soil interception water conservation estimation model.

The vegetation-soil interception water conservation estimation model may include the following equations (9) and (10).

$$V_{max} = CWS + CIS + SMS \qquad (9)$$

$$\begin{cases} Q_{WC} = V_{max} & P_i \geq V_{max} \\ Q_{WC} = P_i & P_i < V_{max} \end{cases} \qquad (10)$$

In the above equations (9) and (10), $V_{max}$ is the maximum forest interception water storage and is measured in mm, CWS is the vegetation canopy interception water storage and is measured in mm, CIS is the litterfall interception water storage and is measured in mm, SMS is the soil water storage and is measured in mm, $Q_{WC}$ is the vegetation-soil interception water conservation and is measured in mm, and $P_i$ is precipitation in an i month and is measured in mm.

The study area surface runoff calculation module 205 may include a study area surface runoff calculation unit configured to calculate the surface runoff in the study area by inputting the monthly precipitation in the processed dataset of the climate element, the monthly snowmelt in the processed dataset of the climate element, the monthly actual evapotranspiration in the processed dataset of the climate element, and the vegetation-soil interception water conservation in the study area into the water balance water conservation estimation model The water balance water conservation model may include the following equation (11).

$$Q_{WC} = Q_{SN} + P - E - R_{Surface}$$

In the above equation (11), $Q_{WC}$ is the vegetation-soil interception water conservation and is measured in mm, P is the monthly precipitation and is measured in mm, E is the monthly actual evapotranspiration and is measured in mm, $R_{Surface}$ is the surface runoff and is measured in mm, and $Q_{SN}$ is the monthly snowmelt and is measured in mm.

The surface runoff in the study area may be calculated by the following equation (12).

$$\begin{aligned} R_{Surface} &= QSN + P - E - Q_{WC} \\ &= Q_{SN} + P - (E + F_C \times LAI \times H_{SV} + \\ &\quad (0.085R_m - 0.1R_0) \times M + SMS) \end{aligned} \qquad (12)$$

In the above equation (12), $Q_{WC}$ is the vegetation-soil interception water conservation and is measured in mm, P is the monthly precipitation in the processed dataset of the climate element and is measured in mm, E is the monthly actual evapotranspiration in the processed dataset of the climate element and is measured in mm, $R_{surface}$ is the surface runoff and is measured in mm, and $Q_{SN}$ is the monthly snowmelt in the processed dataset of the climate element and is measured in mm.

Each embodiment of the present specification is described in a progressive manner, each embodiment focuses on the difference from other embodiments, and the same and similar parts between the embodiments may refer to each other. For a system disclosed in the embodiments, since it corresponds to the method disclosed in the embodiments, the description is relatively simple, and reference can be made to the method description.

Several examples are used for illustration of the principles and implementation methods of the disclosure. The description of the embodiments is used to help illustrate the method and its core principles of the disclosure. In addition, a person of ordinary skill in the art can make various modifications in terms of specific embodiments and scope of application in accordance with the teachings of the disclosure. In conclusion, the content of this specification shall not be construed as a limitation to the disclosure.

Various embodiment of the disclosure may have one or more of the following effects.

In some embodiments, the disclosure may provide a method and a system for estimating a surface runoff based on a pixel scale. The disclosure may break through limitations of a traditional monitoring process, improve regional applicability and accuracy, reduce the difficulty of evaluation, and shorten the evaluation time.

In other embodiments, the disclosure may provide a method and a system for estimating a surface runoff based on a pixel scale. The vegetation-soil interception water conservation estimation model may abandon a traditional formula for calculating a soil water storage by multiplying an average soil thickness by a non-capillary porosity. Instead, the model may use the remote sensing data of soil water content as soil water storage. The result may be more accurate, and the range of monitoring and evaluation may be extended.

In further embodiments, the disclosed methods and systems may deduce a surface runoff calculation formula by combining the vegetation-soil interception water conservation model and the water balance water conservation estimation model, which may implement spatial runoff estimation based on a pixel scale.

In some embodiments, the disclosure may provide a new technical reference and data support for the evaluation of surface water resource characteristics at different time and space scales during ecological restoration and ecological effect evaluation during vegetation restoration.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The invention claimed is:

1. A method for estimating and monitoring a surface runoff, comprising the steps of:
    (1) obtaining an original remote sensing dataset of a climate element in a study area, wherein the original remote sensing dataset of the climate element comprises monthly precipitation, monthly actual evapotranspiration, monthly soil water content, monthly snowmelt, monthly soil thickness, monthly leaf area index, maximum water holding capacity of vegetation, average natural water content of vegetation, and litterfall accumulation,
    wherein the original remote sensing dataset is preprocessed, by at least one operation step selected from the group consisting of format conversion, image correction, cropping, registration, quality inspection, and projection conversion, to obtain a processed dataset;
    (2) calculating a vegetation canopy interception water storage, a litterfall interception water storage, and a soil water storage based on the processed dataset;
    (3) calculating a vegetation-soil interception water conservation in the study area based on an established vegetation-soil interception water conservation estimation model according to the vegetation canopy interception water storage, the litterfall interception water storage, the soil water storage, and the monthly precipitation,
    wherein the vegetation-soil interception water conservation estimation model is established by
        adding up the vegetation canopy interception water storage, the litterfall interception water storage, and the soil water storage, and
        comparing with the monthly precipitation;
    (4) calculating a surface runoff in the study area based on an established water balance water conservation estimation model according to the monthly precipitation, the monthly snowmelt, the monthly actual evapotranspiration, and the vegetation-soil interception water conservation in the study area,
    wherein the water balance water conservation model is established by separately subtracting the monthly actual evapotranspiration and the surface runoff in sequence from a sum of the monthly precipitation and the monthly snowmelt; and
    (5) monitoring the surface runoff in the study area based on the calculated surface runoff in the study area;
    wherein the method is based on a pixel scale.

2. The method of claim 1, wherein step (2) comprises:
    calculating the vegetation canopy interception water storage according to the following equation:

$$CWS = F_C \times LAI \times H_{SV},$$

wherein:
        CWS is the vegetation canopy interception water storage and is measured in mm,
        $H_{SV}$ is the average maximum water holding depth per leaf area and is measured in mm,
        $F_C$ is the vegetation coverage in the processed dataset of the climate element, and
        LAI is the leaf area index in the processed dataset of the climate element;
    calculating the litterfall interception water storage according to the following equation:

$$CIS = (0.085 R_m - 0.1 R_0) \times M,$$

wherein:
        CIS is the litterfall interception water storage and is measured in mm,
        $R_0$ is the average natural water content of vegetation in g/kg,
        $R_m$ is the maximum water holding capacity of vegetation in g/kg, and
        M is the litterfall accumulation in t/hm$^2$; and
    determining that the monthly soil water content in the processed dataset of the climate element is used as the soil water storage.

3. The method of claim 1, wherein:

step (3) comprises calculating the vegetation-soil interception water conservation in the study area by inputting the vegetation canopy interception water storage, the litterfall interception water storage, the soil water storage, and the monthly precipitation in the processed dataset of the climate element into the established vegetation-soil interception water conservation estimation model; and the vegetation-soil interception water conservation estimation model uses the following equations:

$$V_{max} = CWS + CIS + SMS,$$

and $$\begin{cases} Q_{WC} = V_{max} & P_i \geq V_{max} \\ Q_{WC} = P_i & P_i < V_{max} \end{cases},$$

wherein:
- $V_{max}$ is the maximum forest interception water storage and is measured in mm,
- CWS is the vegetation canopy interception water storage and is measured in mm,
- CIS is the litterfall interception water storage and is measured in mm,
- SMS is the soil water storage and is measured in mm,
- $Q_{WC}$ is the vegetation-soil interception water conservation and is measured in mm, and
- $P_i$ is precipitation in an i month and is measured in mm.

4. The method of claim 1, wherein:

step (4) comprises calculating the surface runoff in the study area by inputting the monthly precipitation in the processed dataset of the climate element, the monthly snowmelt in the processed dataset of the climate element, the monthly actual evapotranspiration in the processed dataset of the climate element, and the vegetation-soil interception water conservation in the study area into the water balance water conservation estimation model; and the water balance water conservation model uses the following equation:

$$Q_{WC} = Q_{SN} + P - E - R_{Surface},$$

wherein:
- $Q_{WC}$ is the vegetation-soil interception water conservation and is measured in mm,
- P is the monthly precipitation and is measured in mm,
- E is the monthly actual evapotranspiration and is measured in mm,
- $R_{Surface}$ is the surface runoff and is measured in mm, and
- $Q_{SN}$ is the monthly snowmelt and is measured in mm.

5. A system for estimating and monitoring a surface runoff, comprising:

a climate element original remote sensing dataset obtaining module configured to obtain an original remote sensing dataset of a climate element in a study area, wherein the original remote sensing dataset of the climate element comprises monthly precipitation, monthly actual evapotranspiration, monthly soil water content, monthly snowmelt, monthly soil thickness, monthly leaf area index, maximum water holding capacity of vegetation, average natural water content of vegetation, and litterfall accumulation;

a preprocessing module configured to preprocess the original remote sensing dataset of the climate element to obtain a processed dataset, wherein the preprocessing comprises at least one operation step selected from the group consisting of format conversion, image correction, cropping, registration, quality inspection, and projection conversion;

a correlation factor calculation module configured to calculate a vegetation canopy interception water storage, a litterfall interception water storage, and a soil water storage based on the processed dataset;

a study area vegetation-soil interception water conservation calculation module configured to calculate a vegetation-soil interception water conservation in the study area based on an established vegetation-soil interception water conservation estimation model according to the vegetation canopy interception water storage, the litterfall interception water storage, the soil water storage, and the monthly precipitation, wherein the vegetation-soil interception water conservation estimation model is established by adding up the vegetation canopy interception water storage, the litterfall interception water storage, and the soil water storage, and comparing with the monthly precipitation; and a study area surface runoff calculation module configured to calculate a surface runoff in the study area based on an established water balance water conservation estimation model according to the monthly precipitation, monthly snowmelt, monthly actual evapotranspiration, and the vegetation-soil interception water conservation in the study area, wherein the water balance water conservation model is established by separately subtracting the monthly actual evapotranspiration and the surface runoff in sequence from a sum of the monthly precipitation and the monthly snowmelt;

wherein:
the system is configured to monitor the surface runoff in the study area based on the calculated surface runoff in the study area; and
the system is based on a pixel scale.

6. The system of claim 5, wherein the relation factor calculation module comprises:

a vegetation canopy interception water storage calculation unit configured to calculate the vegetation canopy interception water storage according to the following equation:

$$CWS = F_C \times LAI \times H_{SV},$$

wherein:
- CWS is the vegetation canopy interception water storage and is measured in mm,
- $H_{SV}$ is the average maximum water holding depth per leaf area and is measured in mm,
- $F_C$ is the vegetation coverage in the processed dataset of the climate element, and
- LAI is the leaf area index in the processed dataset of the climate element;

a litterfall interception water storage calculation unit configured to calculate the litterfall interception water storage according to the following equation:

$$CIS = (0.085 R_m - 0.1 R_0) \times M,$$

wherein:
CIS is the litterfall interception water storage and is measured in mm,
$R_0$ is the average natural water content of vegetation in g/kg,
$R_m$ is the maximum water holding capacity of vegetation in g/kg, and
M is the litterfall accumulation in t/hm²; and
a soil water storage determination unit configured to determine that the monthly soil water content in the processed dataset of the climate element is used as the soil water storage.

7. The system of claim 5, wherein:
the study area vegetation-soil interception water conservation calculation module comprises a study area vegetation-soil interception water conservation calculation unit configured to calculate the vegetation-soil interception water conservation in the study area by inputting the vegetation canopy interception water storage, the litterfall interception water storage, the soil water storage, and the monthly precipitation in the processed dataset of the climate element into the established vegetation-soil interception water conservation estimation model; and
the vegetation-soil interception water conservation estimation model uses the following equations:

$$V_{max} = CWS + CIS + SMS,$$

and $$\begin{cases} Q_{WC} = V_{max} & P_i \geq V_{max} \\ Q_{WC} = P_i & P_i < V_{max} \end{cases},$$

wherein:
$V_{max}$ is the maximum forest interception water storage and is measured in mm,
CWS is the vegetation canopy interception water storage and is measured in mm,
CIS is the litterfall interception water storage and is measured in mm,
SMS is the soil water storage and is measured in mm,
$Q_{WC}$ is the vegetation-soil interception water conservation and is measured in mm, and
$P_i$ is precipitation in an i month and is measured in mm.

8. The system of claim 5, wherein:
the study area surface runoff calculation module comprises a study area surface runoff calculation unit configured to calculate the surface runoff in the study area by inputting the monthly precipitation in the processed dataset of the climate element, the monthly snowmelt in the processed dataset of the climate element, the monthly actual evapotranspiration in the processed dataset of the climate element, and the vegetation-soil interception water conservation in the study area into the water balance water conservation estimation model; and
the water balance water conservation model uses the following equation:

$$Q_{WC} = Q_{SN} + P - E - R_{Surface},$$

wherein:
$Q_{WC}$ is the vegetation-soil interception water conservation and is measured in mm,
P is the monthly precipitation and is measured in mm,
E is the monthly actual evapotranspiration and is measured in mm,
$R_{Surface}$ is the surface runoff and is measured in mm, and
$Q_{SN}$ is the monthly snowmelt and is measured in mm.

* * * * *